US012274571B2

(12) United States Patent
Hayashida

(10) Patent No.: US 12,274,571 B2
(45) Date of Patent: Apr. 15, 2025

(54) RADIATION IMAGING SYSTEM, METHOD AND STORAGE MEDIUM

(71) Applicant: CANON KABUSHIKI KAISHA, Tokyo (JP)

(72) Inventor: Shinsuke Hayashida, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 385 days.

(21) Appl. No.: 17/660,714

(22) Filed: Apr. 26, 2022

(65) Prior Publication Data

US 2022/0249039 A1 Aug. 11, 2022

Related U.S. Application Data

(63) Continuation of application No. PCT/JP2020/042962, filed on Nov. 18, 2020.

(30) Foreign Application Priority Data

Nov. 22, 2019 (JP) .................... 2019-211708

(51) Int. Cl.
*A61B 6/42* (2024.01)
*A61B 6/00* (2024.01)
*A61B 6/46* (2024.01)
*G01T 1/17* (2006.01)

(52) U.S. Cl.
CPC ............ *A61B 6/4233* (2013.01); *A61B 6/461* (2013.01); *A61B 6/469* (2013.01); *A61B 6/54* (2013.01); *G01T 1/17* (2013.01)

(58) Field of Classification Search
CPC ....... A61B 6/4233; A61B 6/461; A61B 6/469; A61B 6/54; A61B 6/4258; A61B 6/465; A61B 6/5205; A61B 6/542; G01T 1/17
See application file for complete search history.

(56) References Cited

U.S. PATENT DOCUMENTS 8,600,005 B2 * 12/2013 Suyama ................. G01N 23/04 378/53
9,014,461 B2 4/2015 Hayashida
9,173,634 B2 * 11/2015 Matsunaka .......... A61B 8/0858
9,820,710 B2 * 11/2017 Ohi ..................... A61B 6/5205
9,833,214 B2 * 12/2017 Imamura ........... H01L 27/14607
(Continued)

FOREIGN PATENT DOCUMENTS

JP 7-171142 A 7/1995
JP 2013-70723 A 4/2013
(Continued)

*Primary Examiner* — David P Porta
*Assistant Examiner* — Gisselle M Gutierrez
(74) *Attorney, Agent, or Firm* — VENABLE LLP

(57) ABSTRACT

A radiation imaging system comprises a radiation detector having a plurality of pixels for detecting radiation arrayed in a matrix, a plurality of detecting pixels arranged in a region in which the plurality of pixels are arrayed in the matrix and configured to output a signal corresponding to an amount of irradiation with the radiation; and a processing unit. The processing unit receives weighting information associated with a region of interest in an imaging range and generates determination information for controlling irradiation with the radiation by applying the weighting information to the corresponding signal.

12 Claims, 15 Drawing Sheets

(56) References Cited

U.S. PATENT DOCUMENTS

| | | | |
|---|---|---|---|
| 10,245,003 B2 | 4/2019 | Hayashida | |
| 10,971,532 B2 | 4/2021 | Hayashida | |
| 11,125,702 B2 | 9/2021 | Hayashida | |
| 2004/0183027 A1* | 9/2004 | Passalaqua | G01T 1/1648 250/363.1 |
| 2009/0218529 A1* | 9/2009 | Ohta | G01T 1/24 250/361 R |
| 2010/0252740 A1* | 10/2010 | Akahori | A61B 6/025 250/395 |
| 2010/0308817 A1* | 12/2010 | Vija | A61B 6/545 324/307 |
| 2012/0020541 A1 | 1/2012 | Hayashida | |
| 2013/0077744 A1* | 3/2013 | Kamiya | A61B 6/06 378/62 |
| 2015/0153464 A1* | 6/2015 | Imamura | G01T 7/005 378/207 |
| 2015/0316661 A1* | 11/2015 | Fujiyoshi | H04N 23/30 250/366 |
| 2015/0359498 A1 | 12/2015 | Zou | |
| 2019/0038250 A1 | 2/2019 | Takenaka | |
| 2019/0045612 A1 | 2/2019 | Tamura | |
| 2019/0145911 A1* | 5/2019 | Niwa | A61B 6/544 378/62 |
| 2022/0160319 A1* | 5/2022 | Yamada | G06T 5/50 |
| 2022/0225956 A1* | 7/2022 | Kunieda | A61B 6/542 |
| 2022/0249039 A1* | 8/2022 | Hayashida | A61B 6/469 |

FOREIGN PATENT DOCUMENTS

| | | | | |
|---|---|---|---|---|
| JP | 2016-29987 A | 3/2016 | | |
| JP | 2017-103608 A | 6/2017 | | |
| JP | 2017-196308 A | 11/2017 | | |
| JP | 2018-130334 A | 8/2018 | | |
| JP | 7397636 B2 * | 12/2023 | | A61B 6/4233 |
| JP | 7521099 B2 * | 7/2024 | | A61B 6/542 |

* cited by examiner

RADIATION IMAGING SYSTEM, METHOD AND STORAGE MEDIUM

CROSS-REFERENCE TO RELATED APPLICATIONS

This application is a Continuation of International Patent Application No. PCT/JP2020/042962, filed Nov. 18, 2020, which claims the benefit of Japanese Patent Application No. 2019-211708 filed Nov. 22, 2019, both of which are hereby incorporated by reference herein in their entirety.

BACKGROUND OF THE INVENTION

Field of the Invention

The present invention relates to a radiation imaging system and method and a storage medium.

Background Art

Some radiation imaging apparatuses use a combination of a pixel array provided with conversion elements that convert radiation into electric charge, switching elements such as thin-film transistors, and wiring, a driving circuit, and a reading circuit. One of such apparatuses has a built-in function of detecting irradiation information during irradiation with radiation by a radiation source. This function includes a function of detecting the timing of the start of irradiation with radiation from the radiation source and a function of detecting the amount of irradiation with radiation or integrated amount of irradiation. This function enables automatic exposure control of causing a detection device to monitor an integrated amount of irradiation and control the radiation source to finish irradiation when the integrated amount of irradiation reaches a proper amount.

PTL 1 discloses a technique of deciding an effective sensor effectively used for automatic exposure control based on a histogram generated from signal values from sensor candidates selected in accordance with monitoring conditions.

Although this technique can decide an effective sensor, it cannot designate at which area automatic exposure should be performed.

CITATION LIST

Patent Literature

PTL 1: Japanese Patent Laid Open No. 2016-29987

SUMMARY OF THE INVENTION

In consideration of the above problem, there is provided a radiation imaging system comprising a radiation detector having a plurality of pixels for detecting radiation arrayed in a matrix, a plurality of detecting pixels arranged in a region in which the plurality of pixels are arrayed in the matrix and configured to output a signal corresponding to an amount of irradiation with the radiation, and a processing unit, wherein the processing unit receives weighting information associated with a region of interest in an imaging range and generates determination information for controlling irradiation with the radiation by applying the weighting information to the corresponding signal.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain principles of the invention.

DESCRIPTION OF THE EMBODIMENTS

Figure 1:
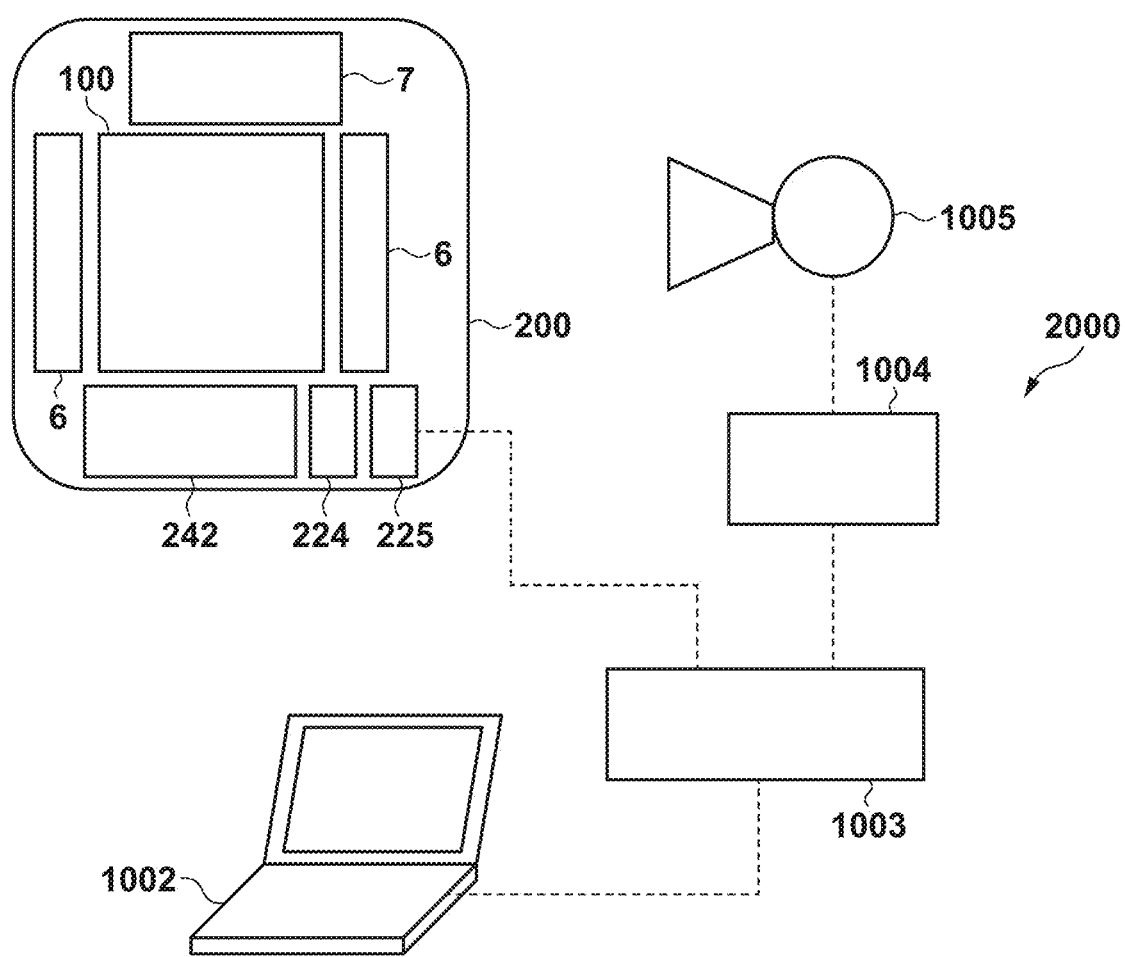
FIG. 1 is a view showing an arrangement related to the automatic exposure control of a radiation imaging system.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

AEC (Auto Exposure Control) will be mainly described below. This technique can be used for radiation dose measurement (monitoring) used for AEC. The imaging apparatus itself may not perform radiation control based on AEC. In addition, this technique may also be used to detect the start of irradiation with radiation and may further be used to detect the end of irradiation with radiation.

Note that this specification will be described by using a PIN type structure as the structure of a conversion element. However, the present invention is not limited to this, and a MIS type structure may be used. Note that radiation can include not only α-rays, β-rays, and γ-rays that are beams generated by particles (including photons) emitted by radioactive decay but also beams having energy equal to or higher than the energy of these beams, for example, X-rays, particle rays, and cosmic rays.

First Embodiment

An outline of a radiation imaging system 2000 will be described first with reference to FIG. 1. The radiation imaging system 2000 includes a radiation source 1005 that applies radiation, a radiation imaging apparatus 200 for capturing a radiation image, and a control system 1002 that inputs imaging conditions and controls the radiation imaging system 2000. The radiation imaging apparatus 200 includes an FPD (Flat Panel Detector) 100 having a plurality of pixels arranged in a matrix on a flat substrate, a reading circuit 7, a communication unit 225, a gate driving circuit 6, a processing unit 242, and a power supply circuit 224. In this case, the FPD (Flat Panel detector) 100 is exemplified but is not limited to this. The FPD 100 functions as a radiation detector obtained by arraying a plurality of pixels for detecting radiation in a matrix.

The gate driving circuit 6 selects, for each row, pixels of the FPD 100 for reading out signals from the pixels, which are arranged in a matrix, and sends signals to the reading circuit 7. The reading circuit 7 amplifies the read signals, A/D-converts the analog signals to digital signals, and sends the signals to a communication relay device 1003 via the communication unit. The communication relay device 1003 relays communication among a radiation controller 1004, the radiation imaging apparatus 200, and the control system 1002. Either a wired or wireless communication scheme may be used. Communication delays or processing delays among the respective units are managed in accordance with a communication scheme, communication contents, and processing contents. Accordingly, each unit can perform communication in consideration of communication delays and processing delays.

An outline of an AEC operation at the time of imaging an object will be described below with reference to FIG. 1. The FPD 100 has detecting pixels including radiation detecting elements for monitoring the amount of irradiation with radiation. Information is set in the control system 1002 before the time of imaging an object so as to stop the radiation source 1005 at a radiation dose A. At this time, the control system 1002 may input ROI (Region of Interest) information in an imaging range. The control system 1002 may input an irradiation time Bms, a tube current CmA, and a tube voltage DkV concerning the radiation source 1005. The operator starts imaging by pressing an exposure switch attached to the radiation source 1005. However, the control system 1002 may control exposure by the radiation source 1005. After the start of exposure by the radiation source, when the integral value of the amount of irradiation with X-rays reaches a radiation dose A', an exposure stop signal is sent to the radiation source 1005 to stop irradiation with X-rays. The radiation dose A' is a value calculated in consideration of the set radiation dose A, a change in X-ray irradiation intensity, and communication delays and processing delays among the respective units. When the irradiation time reaches the set irradiation time Bms, the radiation source 1005 can stop irradiation with X-rays regardless of the presence/absence of an exposure stop signal.

Figure 2:
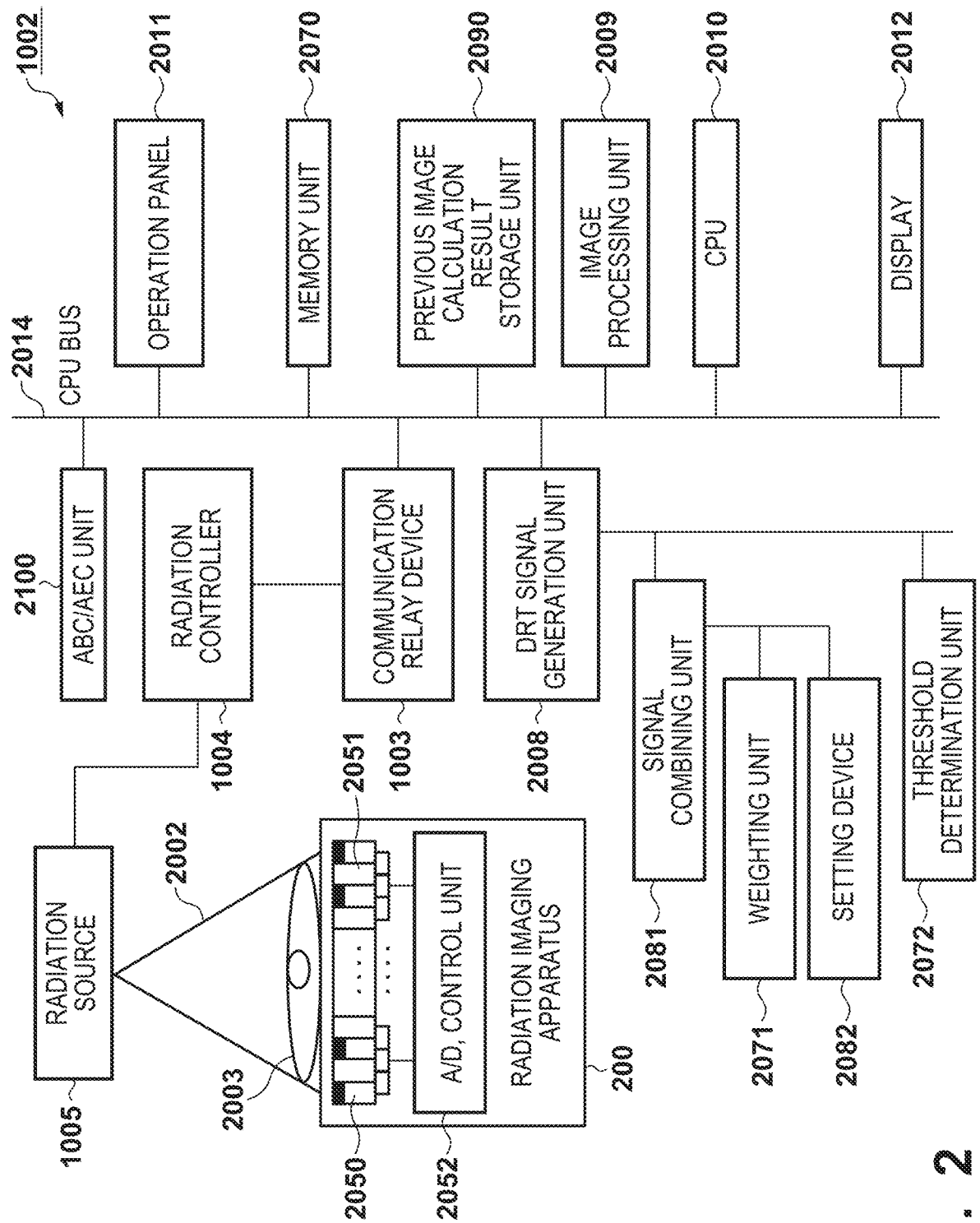
FIG. 2 is a block diagram schematically showing the radiation imaging system.

AEC according to this embodiment will be described next with reference to FIG. 2 which is a block diagram of the radiation imaging system 2000. The control system 1002 includes an operation panel 2011, a CPU 2010 functioning as a processing unit for processing data, a memory unit 2070, and a display 2012 that displays set information and captured images. The control system 1002 communicates data via a CPU bus 2014. In this embodiment, the control system 1002, the radiation imaging apparatus 200, and the radiation controller 1004 can communicate with each other via the communication relay device 1003. The control system 1002, the radiation imaging apparatus 200, and the radiation controller 1004 may respectively include communication units and may communicate with each other via the communication units.

Imaging conditions such as a region of interest as a diagnosis target area are input from the operation panel 2011 functioning as an input unit and set in the control system 1002. The imaging conditions may include the irradiation time B ms, the tube current C mA, and the tube voltage D kV. The imaging conditions are stored in the memory unit 2070. The imaging conditions may be set in the radiation controller 1004 and the radiation imaging apparatus 200 under the control of the CPU 2010. The radiation imaging apparatus 200 includes the FPD 100 having many pixels arranged in a matrix. In this case, light-shielding pixels 2050 and non-light-shielding pixels 2051 are also two-dimensionally arranged in the region in which the pixels of the FPD 100 are arranged in a matrix. In this embodiment, a scintillator converts radiation 2002 applied from the radiation source 1005 onto an object 2003 into visible light. The non-light-shielding pixel 2051 photoelectrically converts the visible light into an electrical signal. On the other hand, the light-shielding pixel 2050 is a pixel light-shielded by a metal or the like. Even when radiation or visible light strikes the light-shielding pixel 2050, light is shielded so as not to be photoelectrically converted. A signal from the light-shielding pixel 2050 can be used for the correction of a dark current and the like.

An AEC operation based on imaging conditions according to this embodiment will be described next. As will be described later, a plurality of detecting pixels including radiation detecting pixels for monitoring radiation doses are also arranged in a region in which the pixels of the FPD 100 are arranged in a matrix. A signal for monitoring a radiation dose from the radiation imaging apparatus 200 and a digital signal for image formation are sent from the communication unit 225 of the radiation imaging apparatus 200 to the communication relay device 1003 and input to the control system 1002. The digital signal for image formation is sent to an image processing unit 2009 under the control of the CPU 2010 to perform processing such as dark current correction, gain correction, and defect correction. The CPU 2010 processes the imaging conditions set in the memory unit 2070 via the operation panel 2011 to generate weighting information for weighting signals from the detecting pixels. This weighting information is sent to a weighting unit 2071 and set in the unit under the control of the CPU 2010. The weighting unit 2071 computes weights based on the weighting information set for signals (monitor signals) from the detecting pixels. An AEC operation is performed based on the weighted signals. The weighting information can be displayed on the display 2012. The weights may be changed from the operation panel.

Weighting will be described below. The region in which the pixels are arranged can be regarded as an imaging range. The imaging range is divided into a plurality of regions (monitor regions). Weighting is performed for each monitor region. Weighting information representing a weight is assigned to each of the plurality of monitor regions. In performing AEC, weighting is performed by applying weighting information to signal values (monitor signal values) from the detecting pixels included in each monitor region. Weighting can be performed according to "weight"*"monitor signal value". Weight assignment and weighting will be described in detail later. Note that a monitor signal value used for weighting may be the average value of signal values from the detecting pixels included in each region or signal values from a predetermined number of detecting pixels selected from the plurality of detecting pixels included in each monitor region or the average value of the signal values.

The weighting unit 2071 weights the monitor signal values input to the control system 1002 from the detecting pixels included in each monitor region based on weighting information for each monitor region. A signal combining unit 2081 can generate determination information for the determination of exposure based on weighted monitor signal values and the weighted average value of the weighed monitor signal values. In this case, a weighted average value can be the value expressed by $(a*1+b*m+c*n+ \ldots +e*p)/(l+m+n+ \ldots +p)$ where a, b, c, ..., e are monitor signal values and l, m, n, ..., p are weights corresponding to the signals.

A setting device 2082 sets thresholds with respect to the minimum value, maximum value, and average value of radiation doses for each monitor region. This setting may be performed via the operation panel 2011. The CPU 2010 may set thresholds based on imaging conditions. A threshold determination unit 2072 determines the radiation dose of irradiation based on a determination formula for determining AEC which is set in the threshold determination unit 2072 and determination information generated by the signal combining unit 2081 and generates determination information for controlling irradiation with radiation. A determination formula may be expressed by a logical formula that can be set based on conditions for the termination of irradiation. Note that the weighting unit 2071 may select a predetermined number of detecting pixels as representatives from the plurality of detecting pixels in a monitor region and perform weighting for signal values from the representatives. This operation can reduce the load of computation processing as compared with the operation of weighting with respect to all the detecting pixels. Detecting pixels may be selected by preparing a device that narrows down the selected detecting pixels to detecting pixels located at necessary positions. In this case, the signal combining unit 2081, the weighting unit 2071, and the threshold determination unit 2072 may be parts of the functions of the CPU 2010 as a processing unit, and the configuration for performing these processes may be called a processing unit. The above has described the case in which the control system 1002 performs weighting and determination on AEC. However, the radiation imaging apparatus 200 may have these functions. Weighting information corresponding to a plurality of monitor regions may be input to the radiation imaging apparatus 200 to generate determination information by computing weights corresponding to signals from detecting pixels in each monitor region, thereby performing AEC based on a determination formula. Alternatively, the radiation imaging apparatus 200 may output weighted signals.

Figure 3:
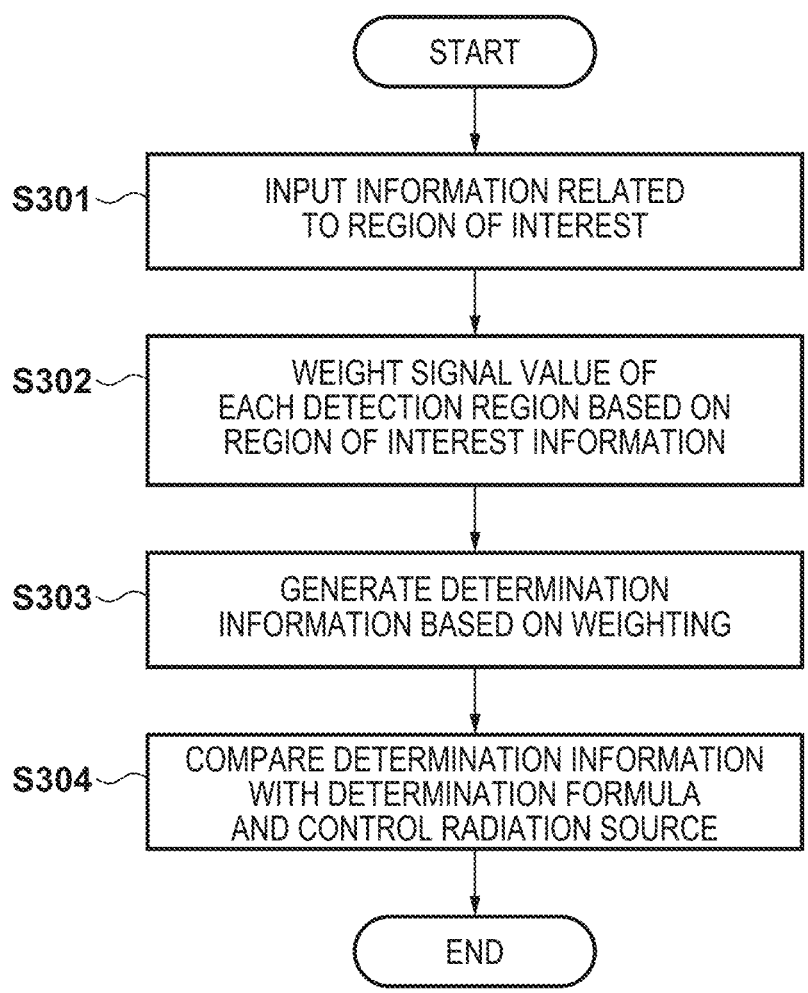
FIG. 3 is a flowchart for radiation imaging.

Outlines of weighting using information concerning a region of interest and determination on AEC will be described with reference to FIG. 3. The radiographer inputs information (region-of-interest information) related to a region of interest via the operation panel 2011 before imaging (step S301). Information may be input from a hospital system. A region of interest may be a region, of the plurality of regions obtained by dividing an imaging range, which includes a diagnosis target. Radiation dose determination at the time of AEC is performed by causing the weighting unit 2071 to compute weighting information for a monitor signal value from each of a plurality of divided imaging ranges (step S302). Weighting computation may be performed for monitor signal values from a predetermined number of detecting pixels selected as representatives from the detecting pixels in each monitor region instead of being performed for all monitor signal values for each monitor region. Alternatively, the weighting unit 2071 may perform weighting for the average value of monitor signal values from a plurality of detecting pixels in a monitor region. The signal combining unit 2081 then generates determination information based on the weighted monitor signal value (step S303). The threshold determination unit 2072 compares the determination information with the determination formula set based on the maximum value and minimum value of the monitor signal values and a threshold (step S304). When the determination information satisfies conditions for the stop of irradiation based on the determination formula, a stop signal for stopping the irradiation with radiation is transmitted to the radiation controller 1004, thereby stopping the irradiation. The CPU 2010 may execute the processing performed by the weighting unit 2071, the signal combining unit 2081, and the threshold determination unit 2072 based on programs stored in the memory unit 2070.

Figure 4:
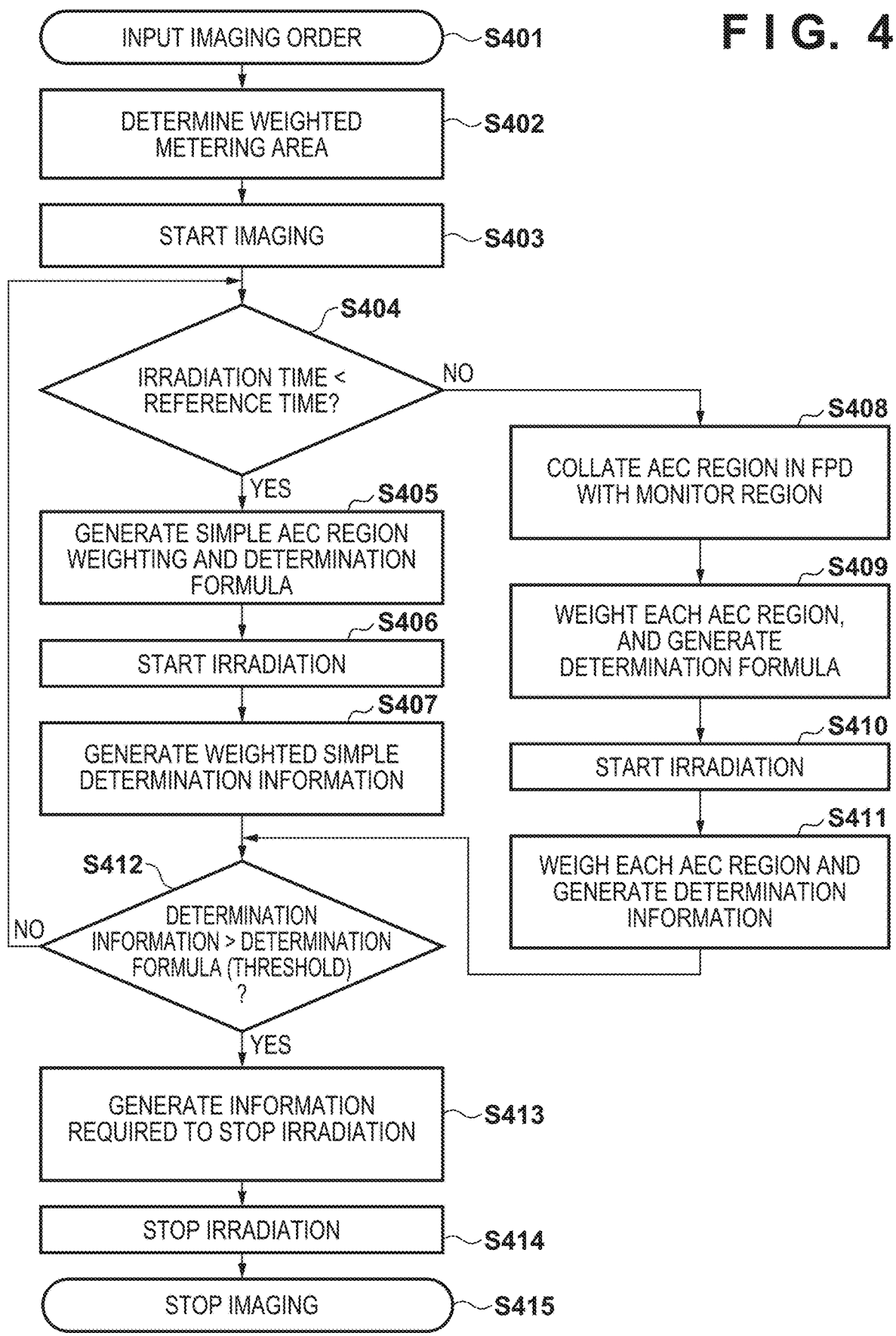
FIG. 4 is a flowchart for radiation imaging.

An outline of the operation based on an imaging order will be described with reference to FIG. 4 by exemplifying the case in which the control system 1002 performs the operation. The hospital system or the radiographer inputs an imaging order to the radiation imaging system (step S401). The imaging order includes inspection information including inspection contents. This inspection information includes an imaging target area at the time of radiation imaging and an imaging purpose. In addition, the inspection information may include parameter information used at the time of imaging, information concerning an imaging execution method, and information concerning an imaging environment. An imaging target area and an imaging purpose can be designated with respect to the radiation imaging system based on the information included in the imaging order. The imaging target area may be decided in accordance with a diagnosis target. The imaging purpose is input like a regular health checkup.

The following additional information may be input: information attached to the imaging order at the time of inputting an imaging order; information at the time of previous imaging; and information indicating that this region in particular is to be an imaging target. An imaging order may include information of a region of interest. The methods of inputting an imaging order and additional information include a method of inputting words representing an imaging range and an imaging purpose and a method of selecting and inputting a predetermined portion of an image upon displaying a sample image. These methods may also include a method of displaying and selecting a plurality of imaging regions. These pieces of input information are imaging conditions. The CPU 2010 determines an emphasis area as a portion to be controlled upon emphatically measuring exposure based on imaging conditions (step S402).

When the radiation imaging system 2000 starts an imaging operation (step S403), the CPU 2010 determines an irradiation time based on imaging conditions before irradiation with radiation (step S404). The irradiation time of radiation can be changed depending on the specification or purpose of the radiation source 1005. A radiation source with low output power is designed to obtain an image by irradiation for about 100 ms to 1,000 ms, whereas a radiation source with high output power is designed to obtain an image by irradiation for about 1 ms to 10 ms. If the CPU 2010 determines that the irradiation time is shorter than a reference time (YES in step S404), the CPU 2010 prepares a simple weighting formula and a simple determination formula (step S405) and starts irradiation while controlling the radiation source (step S406), thereby performing simple AEC. In the simple AEC, the weighting unit 2071 uniformly weights monitor signal values. The signal combining unit 2081 generates determination information based on the weighted monitor signal values (step S407). Upon determining based on the determination formula that the determination information exceeds a threshold (S412), the threshold determination unit 2072 notifies the CPU 2010 of the corresponding information. Upon receiving the notification, the CPU 2010 generates a stop signal required to stop the irradiation of the radiation (step S413) and gives an instruction to stop the irradiation to the radiation controller 1004. Upon receiving the instruction, the radiation controller 1004 stops the irradiation by the radiation source (step S414) and terminates the imaging (step S415).

Upon determining that the irradiation time is longer than the reference time (NO in step S404), the CPU 2010 collates the position of a monitor region with the position of a detecting pixel arranged in the FPD 100 (step S408). This collation links the position of the monitor region to the position of the detecting pixel arranged in the FPD 100. The CPU 2010 then generates a weight (weighting information) corresponding to a signal from the detecting pixel in the monitor region and a determination formula for the determination of the stop of irradiation based on imaging conditions (step S409). In this case, the radiographer may set a weight in the weighting unit 2071 for each region via the operation panel 2011. When the radiation source 1005 starts irradiation with radiation (step S410), the weighting unit 2071 performs weighting computation for a monitor signal value from the detecting pixel included in the corresponding region based on the weighting information. The signal combining unit 2081 generates determination information based on the weighted monitor signal value (step S411). The threshold determination unit 2072 determines whether the value of the determination information exceeds the threshold. Upon determining that the value of the determination information has exceeded the threshold (condition) of the determination formula (step S412), the threshold determination unit 2072 notifies the CPU 2010 that the value of the determination information has exceeded the threshold. Upon receiving the notification, the CPU 2010 generates a stop signal for controlling irradiation with radiation (step S413). The CPU 2010 controls the radiation controller 1004 based on the stop signal to stop the irradiation with radiation and terminate the imaging (steps S414 and S415). The determination formula for determining the stop of irradiation will be described in detail later. The control system 1002 or the radiation imaging apparatus 200 may perform these processes. The radiation imaging apparatus 200 can also perform some of the processes. The CPU 2010 may perform all or some of the processes by the signal combining unit 2081, the weighting unit 2071, and the threshold determination unit 2072. Note that the order of steps in this procedure may be changed. That is, step S404 may be performed between steps S401 and S402 or between steps S402 and S403. In addition, step S408 may be performed following step S402. Even if the irradiation time is shorter than the reference time, irradiation may be performed to associate the monitor region with the detecting pixel arranged in the FPD 100. Note that the reference time can be decided in accordance with the specification of the radiation source or the processing time of the CPU 2010.

Figure 5:
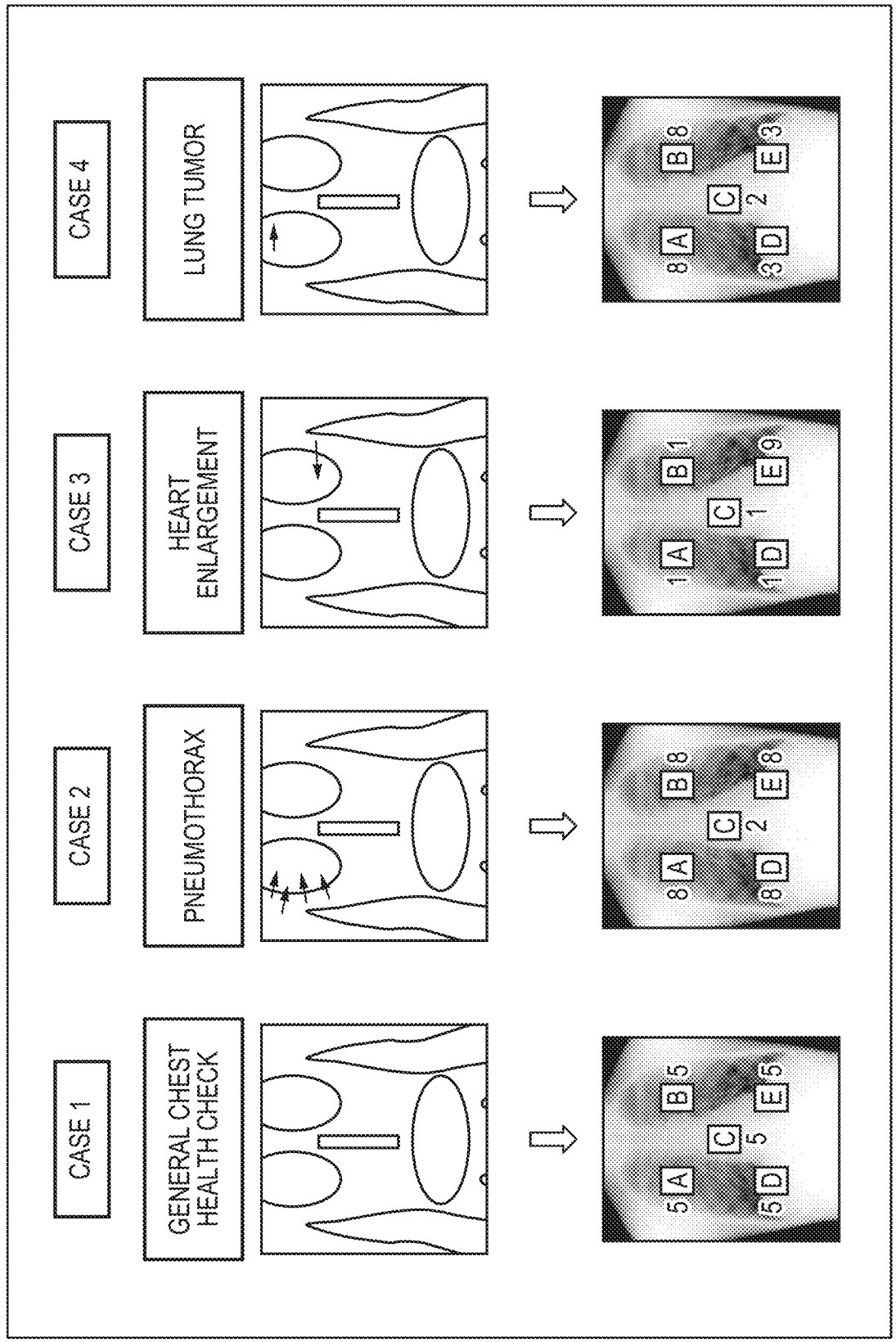
FIG. 5 is a view showing an example of weighting according to emphasis areas.

An example of weighting for an emphasis area to be diagnosed in particular in a monitor region in an imaging range will be described with reference to FIG. 5. Monitor regions as AEC targets will be described by exemplifying five regions. However, monitor regions may be 3×3=9 regions or 5×5=25 regions. Alternatively, an imaging target region may be arranged in a unique place. The value of a weight for a monitor signal value of a monitor region and a pattern are decided based on imaging conditions such as a region of interest and an imaging purpose. As in the case shown in the upper part of FIG. 5, while an upper body pattern is displayed on the display, the radiographer may select a target area as a region of interest from options A to E via an instruction device in accordance with a purpose. When the imaging conditions include a general chest health check as in case No. 1, the whole chest region becomes a region of interest. Weights associated with the region of interest become the same value as a whole. Determination information for the execution of AEC may be obtained based on the value obtained by uniformly weighting the respective monitor signal values from five monitor regions. When the imaging conditions include a pneumothorax check as in case No. 2, lung fields are selected as regions of interest. In this case, weights for portions related to the regions of interest may be increased. The weights for monitor regions A, B, D, and E each may be set to 8, and the weight for monitor region C may be set to 2, thereby generating determination information by applying the weights to the monitor signal values obtained in the respective areas. When a cardiomegaly check is to be made as in case No. 3, the weight for a monitor region of a given portion of the heart may be increased as compared with the other portions. In this case, the weights for monitor regions A, B, C, and D each are set to 1, and the weight for monitor region E is set to 9. It is possible to increase the weight for a specific region in checking a specific portion of interest or follow-up after surgery, as indicated by the arrow in case No. 2 to No. 4. Note that in the case shown in FIG. 5, there are five monitor regions. However, the number of monitor regions may be increased or decreased. In addition, as shown at the bottom of FIG. 5, the set weight values may be displayed on the display 2012 to allow the radiographer to check the weights and correct a weight via the operation panel 2011.

A weighting calculation example will be described with reference to FIGS. 6A and 6B. This is the case in which whether to perform weighting in a normal way or simple way is determined whether the irradiation time determined from the imaging conditions is longer or shorter than the reference time. In this case, when the amount of irradiation per unit time is large and the irradiation time is short, monitor signal values are simply and uniformly weighted. When the amount of irradiation per unit time is small and the irradiation time can be prolonged, weighting is performed by applying a weighting coefficient assigned to each region to each monitor signal value in a monitor region.

When weighting is performed, the values included in determination information after the weighting differ for an image having the same pixel values (signal values). The case in which the irradiation time is short will be described with reference to FIG. 6A. When strong radiation is applied even for a short irradiation time, radiation may be applied beyond the dynamic range of the FPD 100 in which imaging can be performed. In general, when radiation is applied beyond the saturated dose, the FPD 100 has difficulty in forming an image from signals obtained from the pixels. Accordingly, when the irradiation time is shorter than the reference time, the average of monitor signal values from all the monitor regions may be used as determination information and compared with a threshold to determine whether to stop the irradiation. In this case, the computation can be simplified, and hence determination information can be obtained even in a short computation time, thereby reducing excessive irradiation with radiation.

For the sake of explanation, assume that monitor signal values from monitor regions A, B, C, D, and E are A: 2000, B: 2000, C: 400, D: 300, and E: 300. In this case, since the same weights are assigned to the respective monitor regions, the average value of the monitor signal values from all the monitor region is 1000=(2000+2000+400+300+300)/5.

Figure 6A:
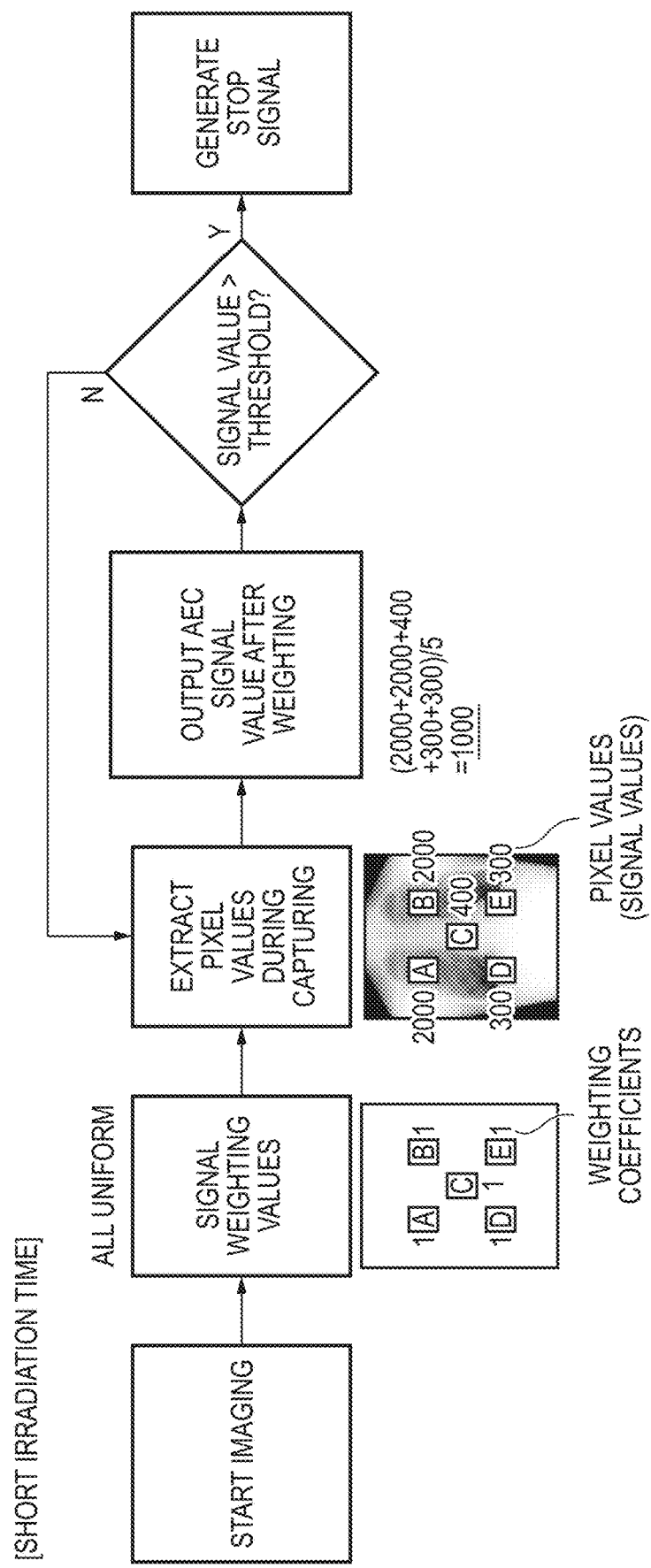
FIG. 6A is a view showing an example of weighted computation according to emphasis areas.
Figure 6B:
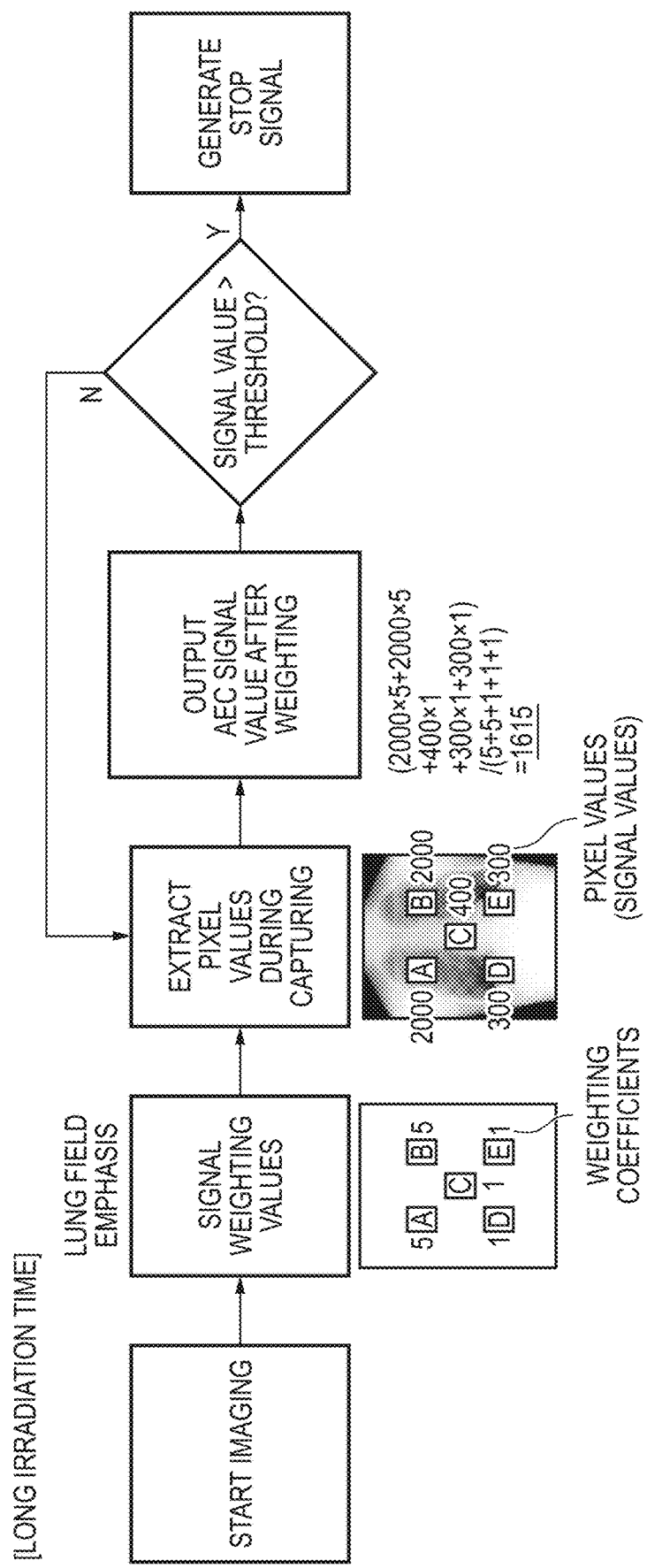
FIG. 6B is a view showing an example of weighted computation according to emphasis areas.

FIG. 6B shows a case in which the irradiation time is longer than the reference time. When the irradiation time is long, sufficient time is afforded for computation, and hence it is possible to perform AEC suitable for monitor regions based on the imaging conditions by measuring the doses of radiation applied to emphasis areas. Assume that in this case, the lung fields are the emphasis areas, and the degree of interest in other monitor regions is low.

Assume that in this case, the current radiation dose has reached a radiation dose at which the same pixel value (signal value) as that in FIG. 6A is obtained from each monitor region. The monitor signal values are A: 2000, B: 2000, C: 400, D: 300, and E: 300 as in FIG. 6A. Weighting is performed according to following weighting coefficients: A: 5, B: 5, C: 1, D: 1, and E: 1. Accordingly, the weighted average value of signals from all the monitor regions is 1615=(2000*5+2000*5+400*1+300*1+300*1)/(5+5+1+1+1). The comparison between the average value of the signal values in FIG. 6A and the average value of the signal values in FIG. 6B indicates that the average value in the case shown in FIG. 6B greatly differs from that in the case shown in FIG. 6A when the same dose of radiation is applied. When weighting is performed, the influence of the radiation dose on the larger weighted region is larger on the determination information.

This comparison indicates that the radiation dose in a region including an emphasis area (weighted metering area) in the case shown in FIG. 6A does not reach a condition for stopping irradiation with radiation unless the radiation dose is as large as 1.6 times the radiation dose in the case shown in FIG. 6B. In the case shown in FIG. 6B, when the current dose reaches the radiation dose required for the lung field, the irradiation can be stopped based on the determination information. Accordingly, it is possible to generate information required to stop irradiation with a radiation dose about 0.6 times that in the case shown in FIG. 6A. That is, increasing the weight for an emphasis area as compared with the weights for the other monitor regions can control the radiation source at a proper radiation dose with respect to the emphasis area. Although this embodiment has been described by exemplifying the five monitor regions, the range in which the present invention can be applied can be used for monitor regions smaller in number than all the pixels.

Figure 7:
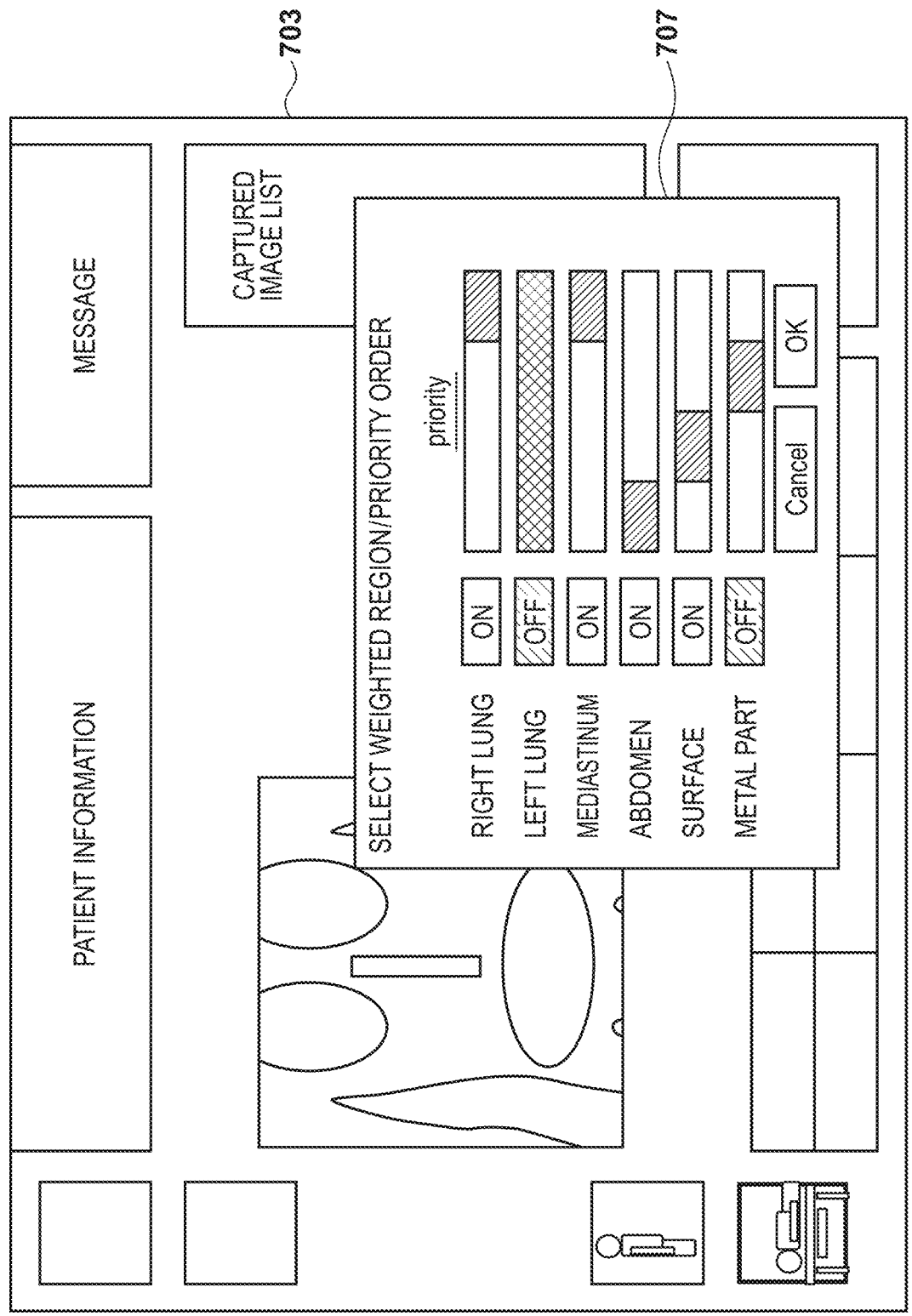
FIG. 7 is a view showing an example of an input screen showing emphasis areas.

FIG. 7 shows an example of a screen 703 showing an example of imaging conditions displayed on the display 2012 when imaging conditions for imaging are input in this embodiment. A window 707 in the screen 703 displays "ON" and "OFF" indicating whether to set an exposure limit for each monitor region and priorities. The window 707 also indicates the names of the imaging target regions. This makes it possible to select a weighted metering area from the displayed regions. Weights can be set by intuitively inputting priorities on the screen. The radiographer may select a displayed item using a mouse or keyboard. Clinical image examples and diagrams may be displayed to allow the radiographer to designate an emphasis area by using the touch panel, the mouse, or the like. Advantages in designating on the screen are that a direct input operation can be performed because the radiographer can designate a position where radiation is actually applied, and the radiographer can perform an intuitive input operation. Set imaging conditions may be displayed on the display 2012 in accordance with an instruction from the radiographer. Note that the display and input methods are not limited to those described above.

The radiographer is not always a person who diagnoses captured images. For this reason, when the degree of freedom of the method of setting emphasis areas is high, recognition differences may occur between the settings made by the radiographer and the instructions issued by the diagnostician. This may result in selecting a wrong emphasis area. Accordingly, displaying emphasis areas and weights in words to allow selection or using a device that allows the operator to input emphasis areas and weights in numerical values (coordinates) makes it possible to visualize options and numbers, thereby reducing the recognition differences between the radiographer and the diagnostician. This produces the merit of enabling imaging operations with good reproducibility even if the radiographer and the diagnostician are not the same person. The device used for input operations on the display may also be equipped with a device that displays emphasis areas and the like in words to allow selection of weights or a device that inputs words, thereby allowing selection of an input method at the time of setting conditions or imaging.

An example of generating determination information based on weighting information and determining the stop of irradiation based on the determination information and a determination formula will be described with reference to FIGS. 8A and 8B. In this case, AEC is determined based on, for example, set upper and lower limit thresholds for the value obtained from each monitor region and a signal value by combining weighted monitor signal values. This is because the reason why upper and lower limit thresholds are set is that only using the average of monitor signal values after weighting may cause shadow detail loss or highlight detail loss. Using upper or lower limit threshold for AEC can reduce the possibility of the generation of a saturated region due to an excessively large dose or conversely can reduce the possibility that X-ray quantum noise becomes dominant due to an excessively small dose. It is possible to use only an upper limit threshold or a lower limit threshold in accordance with the purpose of imaging and the like. In addition, an overall appropriate image can be obtained by combining monitor signal values from a plurality of monitor regions and performing overall determination.

Figure 8A:
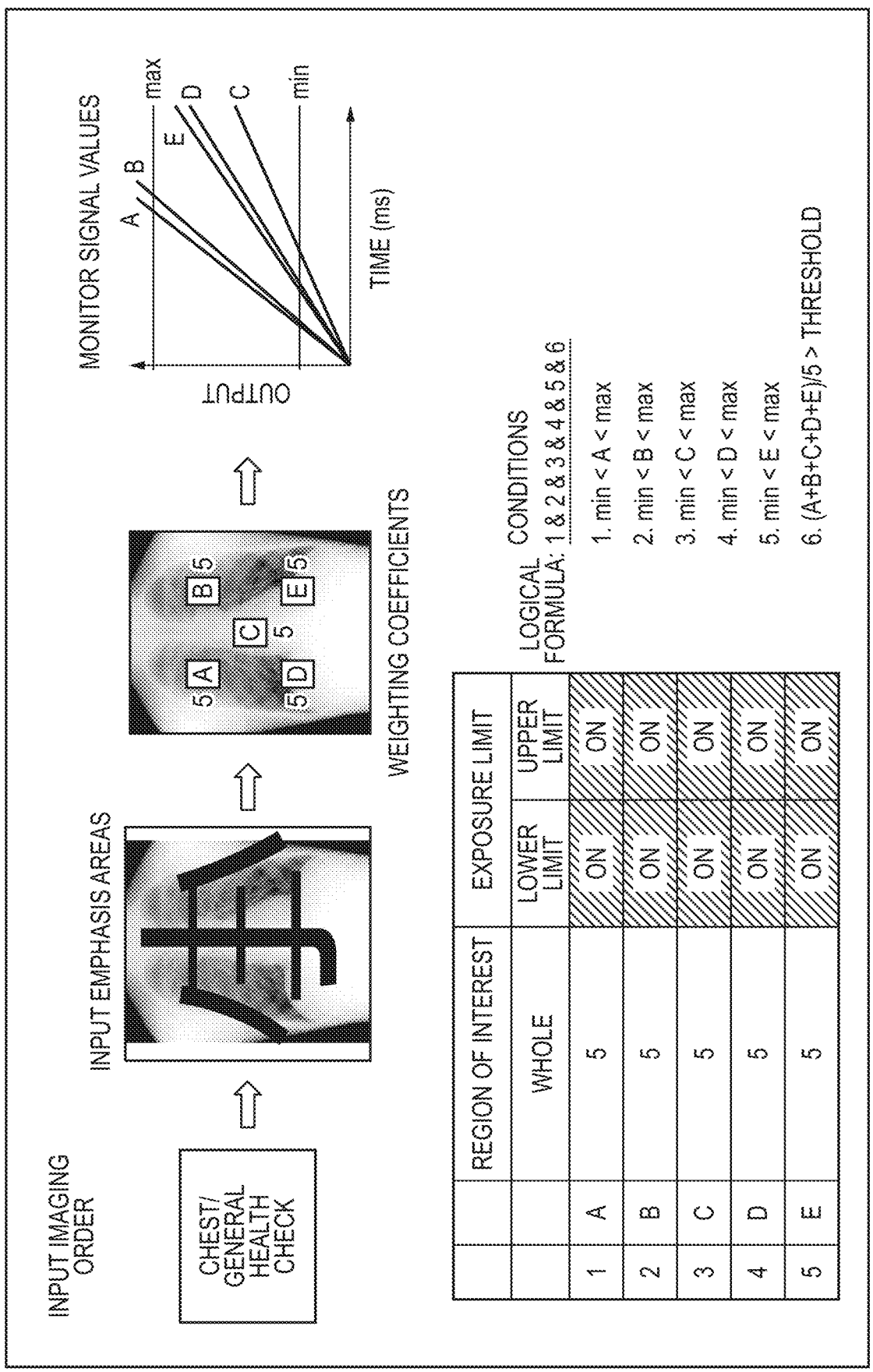
FIG. 8A is a view showing an example of a determination method based on signal values.

FIG. 8A is a view for explaining a case in which determination is performed when the imaging order is a general chest health check. Upon receiving the imaging order of the general chest health check, the radiographer inputs, to the control system 1002, a region related to an imaging target area based on check points to be noted in terms of imaging. In this case, the following will exemplify a case in which the pattern obtained by superimposing the shapes of "|", "=", and "J" on the image is input, as a pattern that is originally used to explain the movement of the line of sight at the time of radiogram interpretation. This pattern can be input from the screen by using a touch panel and a mouse. If it is determined based on the input pattern that the overall image is of interest, the uniform weight of "5" is set for each of all monitor regions A, B, C, D, and E. In addition, setting upper limit values and lower limit values in all monitor regions A, B, C, D, and E makes it possible to perform imaging while preventing an image from being saturated in each monitor region due to an excessively large dose or preventing noise from dominating an image due to an excessively small dose. Assume that the monitor signal values from monitor regions A, B, C, D, and E each monotonically increase with the lapse of the irradiation time. When weights for a plurality of regions are the same, weighting computation may be simply performed to calculate an average.

Assume that in this case, the determination conditions for monitor signal values A to E from the five monitor regions are 1. min<A<max, 2. min<B<max, 3. min<C<max, 4. min<D<max, and 5. min<E<max. Assume also that the overall determination condition is 6. (A+B+C+D+E)/5>threshold. These conditions, namely, conditions 1. to 6., can be determination criteria for the stop of irradiation. These conditions may be combined with a logical formula to form a determination formula. FIG. 8A shows a case in which when the determination information satisfies the AND conditions in conditions 1. to 6., the radiation controller is controlled to stop the irradiation. Another determination formula may be generated so as to output information required to stop radiation to prevent highlight detail loss when at least one of monitor signal values A to E exceeds "max" or condition 6. is satisfied. The default setting of the determination formula may be configured to AND all the conditions, while another determination formula can be selected as an option.

Figure 8B:
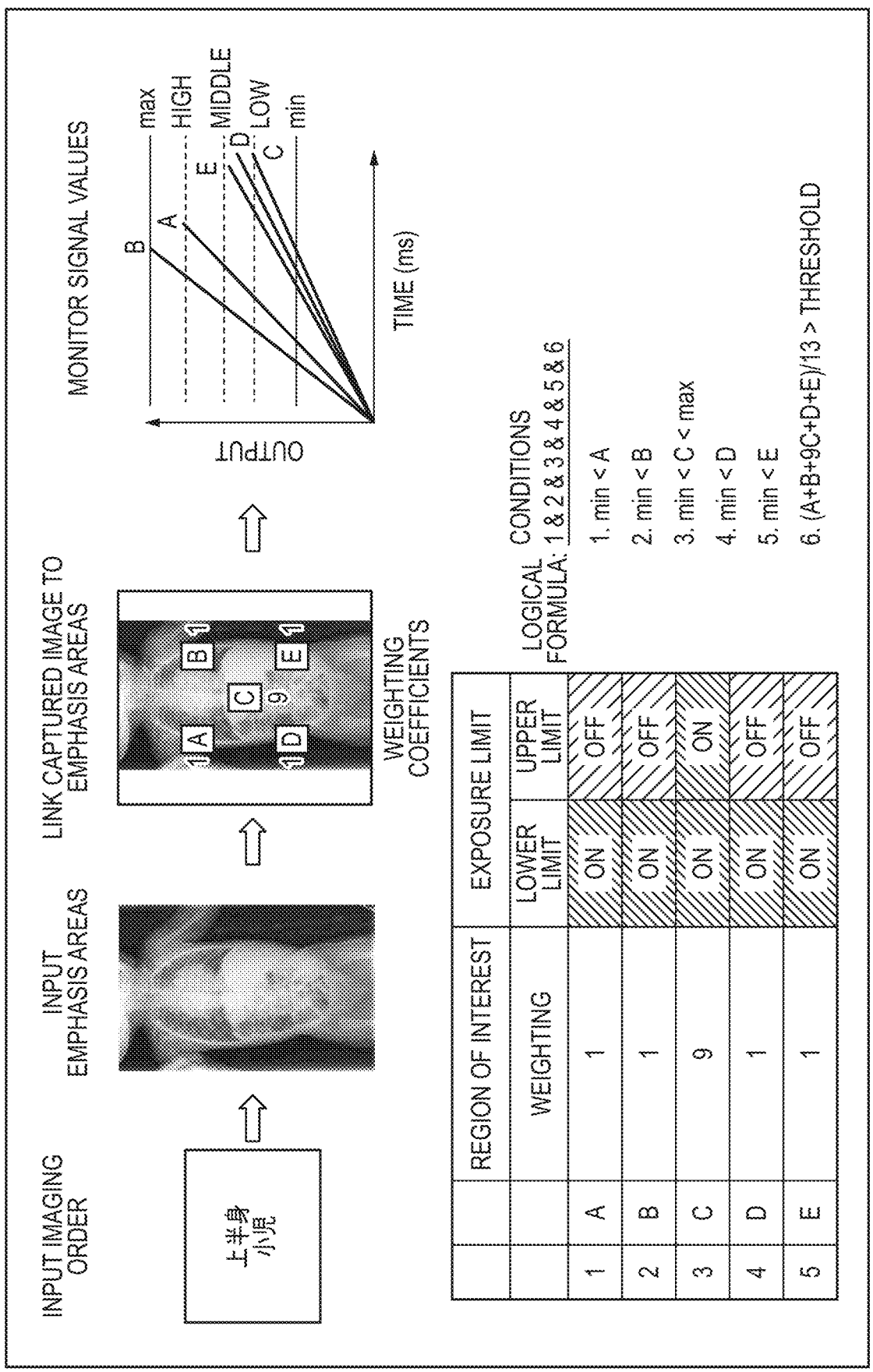
FIG. 8B is a view showing an example of a determination method based on signal values.

FIG. 8B is a view for explaining a case in which an imaging target is a child. Upon receiving an imaging order, the radiographer inputs a weighted metering area related to a region of interest based on a check point to be noted in imaging. Although the radiographer may input a weighted metering area from an image on the input unit, this embodiment will exemplify a case in which the radiographer has input the area in the words "child/upper body". Children greatly differ in body size, and hence it is preferable to allow the radiographer to additionally input, for example, body height/body weight/age/physical size information as supplementary information. In addition, if the radiographer can input information indicating whether the purpose of imaging is to diagnose an injury or disease, more suitable imaging can be performed.

When an imaging range is to be narrowed down in accordance with information such as the purpose of imaging and a region of interest, radiation doses in all the regions of the FPD 100 sometimes need not be values that allow visualization. Referring to FIG. 8B, the weight in monitor region C is set as large as "9" to narrow down the imaging target region. The weights in monitor regions A, B, D, and E are set to "1". When it is just required to acquire a suitable image in monitor region C as in this case, the radiation doses for monitor regions A, B, D, and E may sometimes reach the saturated dose or more in the FPD 100. In this case, in each of monitor regions A, B, D, and E, the upper limit value setting of the exposure limit may be "OFF".

Assume that in this case, the determination conditions for monitor signal values A to E from the respective monitor regions are 1. min<A, 2. min<B, 3. min<C<max, 4. min<D, 5. min<E, and 6. (A+B+9*C+D+E)/13>threshold. In this case as well, when it is preferable to stop irradiation if the determination information satisfies all the conditions, namely, condition 1. to condition 6., the logical formula is configured to AND condition 1. to condition 6. Although this embodiment has been described by exemplifying the five monitor regions, the applicable range of the present invention can also be applied to signal regions smaller in number than the total number of pixels. The number of monitor regions may be set as needed.

Figure 9:
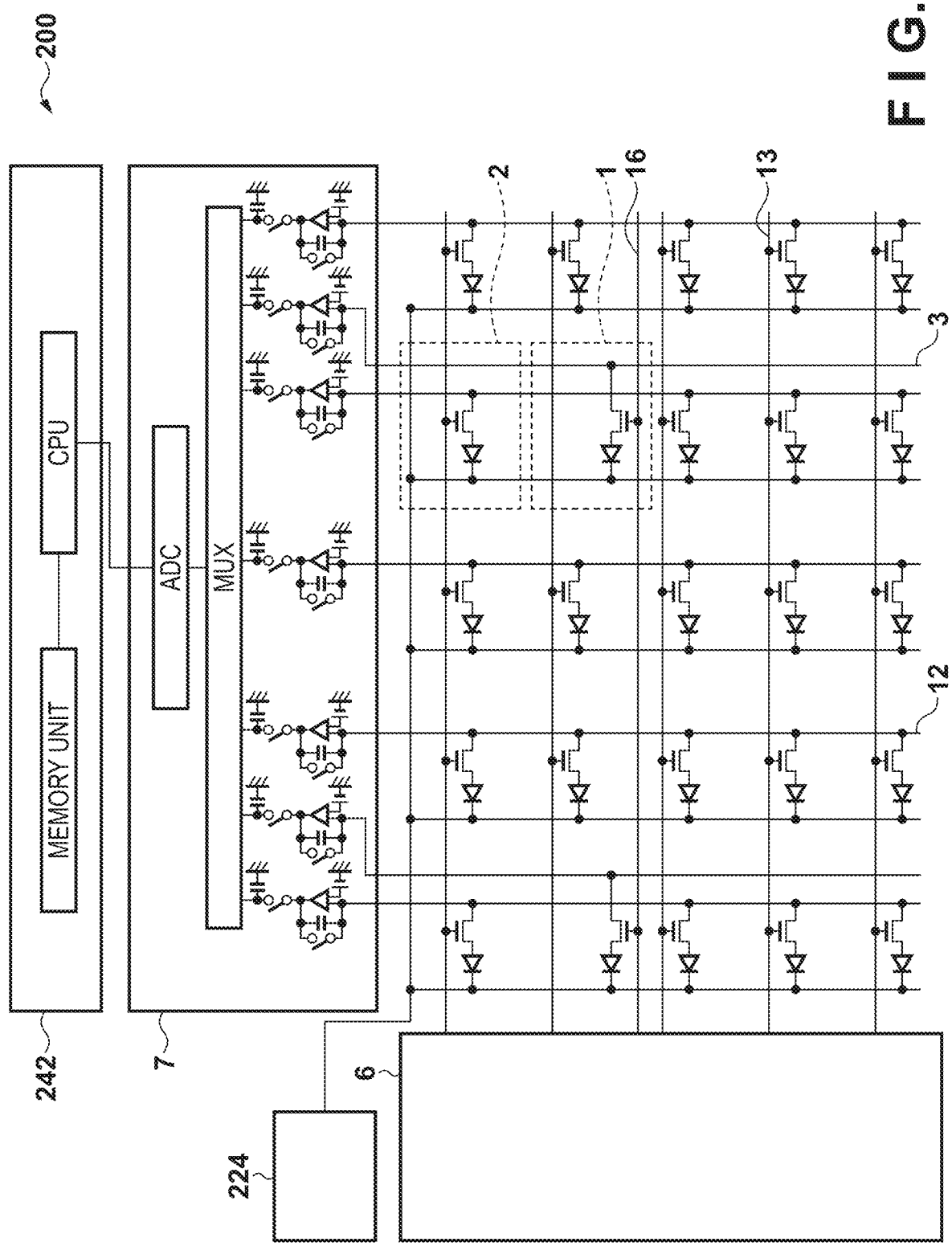
FIG. 9 is a schematic circuit diagram of a radiation detector.

The radiation imaging apparatus 200 will be described next with reference to FIG. 9. FIG. 9 shows a case in which 5×5 pixels are provided in the pixel region in which the pixels are arranged in a matrix. However, the number of pixels is not limited to this. In the pixel region, pixels 2 for capturing a radiation image are arranged in a matrix. A detecting pixel 1 for detecting a radiation dose is arranged instead of the pixel 2 in part of the pixel region. The detecting pixel 1 may be used to detect the start and end of irradiation with radiation in addition to monitoring the amount of irradiation during a period in which radiation is applied. A control wire 16 drives the gate of the switch of the detecting pixel 1 to control reading. A control wire 13 controls reading by the pixel 2 for image formation. The signal generated by the detecting pixel 1 is transferred from a detecting signal line 3 to the reading circuit 7 to read a signal amount. Acquiring information from the detecting pixel 1 makes it possible to monitor the dose of radiation applied in the region in which the pixel 2 near the detecting pixel 1 is arranged. A monitor region for monitoring a radiation dose can be selected by controlling the control wire 16 so as to select a predetermined row and select a detecting signal line for reading a monitor signal from the detecting pixel 1. Selecting the control wire 16 and the detecting signal line 3 can collate the weighted metering area with the monitor region and read a monitor signal.

When the radiation imaging apparatus 200 is to perform AEC (Automatic Exposure Control), the processing unit 242 performs determination for AEC by receiving weighting information and a determination formular from the control system 1002. The processing unit 242 collates the position of the monitor region with the position of the weighted metering area and measures the dose of radiation for each region. Subsequently, the processing unit 242 generates determination information by using weighting information, compares the information with the determination formula, and calculates the time at which a preset amount of irradiation is reached. The processing unit 242 transmits a stop signal to the communication relay device 1003 via the communication unit 225 in consideration of delays caused in communication and processing. The transmitted stop signal controls the radiation controller 1004 via the communication relay device 1003 to stop the irradiation with radiation.

Figure 10:
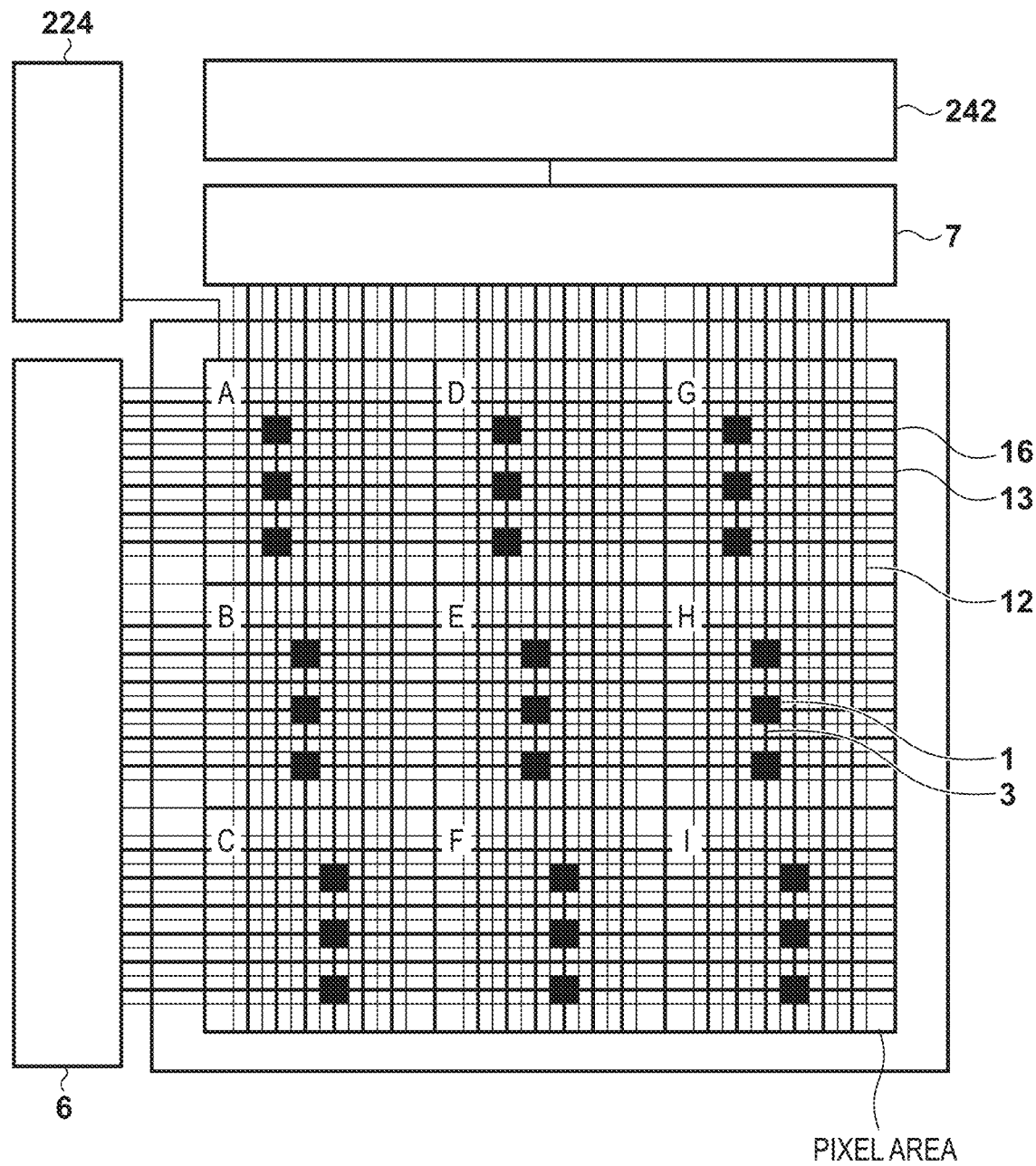
FIG. 10 is a view showing the placement of radiation detecting elements of the radiation detector.

The detecting pixel 1 arranged in the pixel region of the radiation imaging apparatus 200 will be described with reference to FIG. 10. In this case, the pixel region of the FPD 100 is divided into nine monitor regions A to I. A plurality of detecting pixels 1 are arranged in each region. The driving of each detecting pixel 1 is controlled to allow the detection of the dose of radiation applied for each monitor region. The monitor signal read from the detecting pixel 1 is transferred to the processing unit 242 via the reading circuit 7. The processing unit 242 monitors the amount of irradiation and can output a monitor signal for each monitor region from the detecting pixel 1 to the outside of the system at the time of an AEC operation. When the radiation imaging apparatus 200 is to perform AEC, it is possible to issue an instruction to the radiation controller 1004 so as to stop the irradiation with radiation at the time when the radiation dose becomes a proper dose based on a monitor signal.

As described above, the present invention can associate a region for detecting a radiation dose for automatic exposure with a part of an object, and hence is advantageous in visualizing a region to be diagnosed, thereby reducing the load on the radiographer or patient.

Second Embodiment

The second embodiment will be described next. In this embodiment, to prepare for imaging, a sample image is displayed before imaging for the purpose of checking imaging conditions for irradiation with radiation. Portions different from the first embodiment will be mainly described below.

Figure 11A:
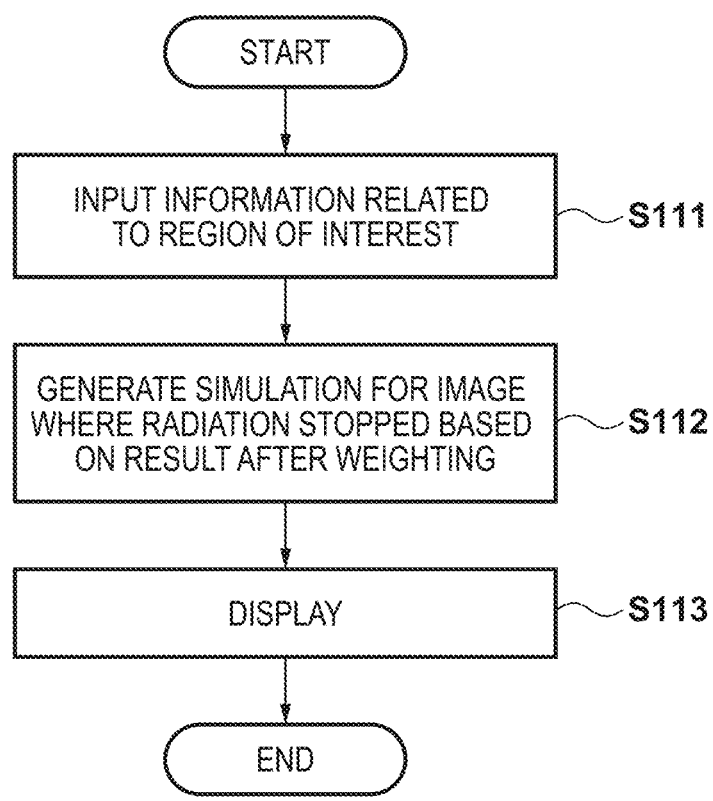
FIG. 11A is a schematic flowchart for deciding imaging conditions.
Figure 11B:
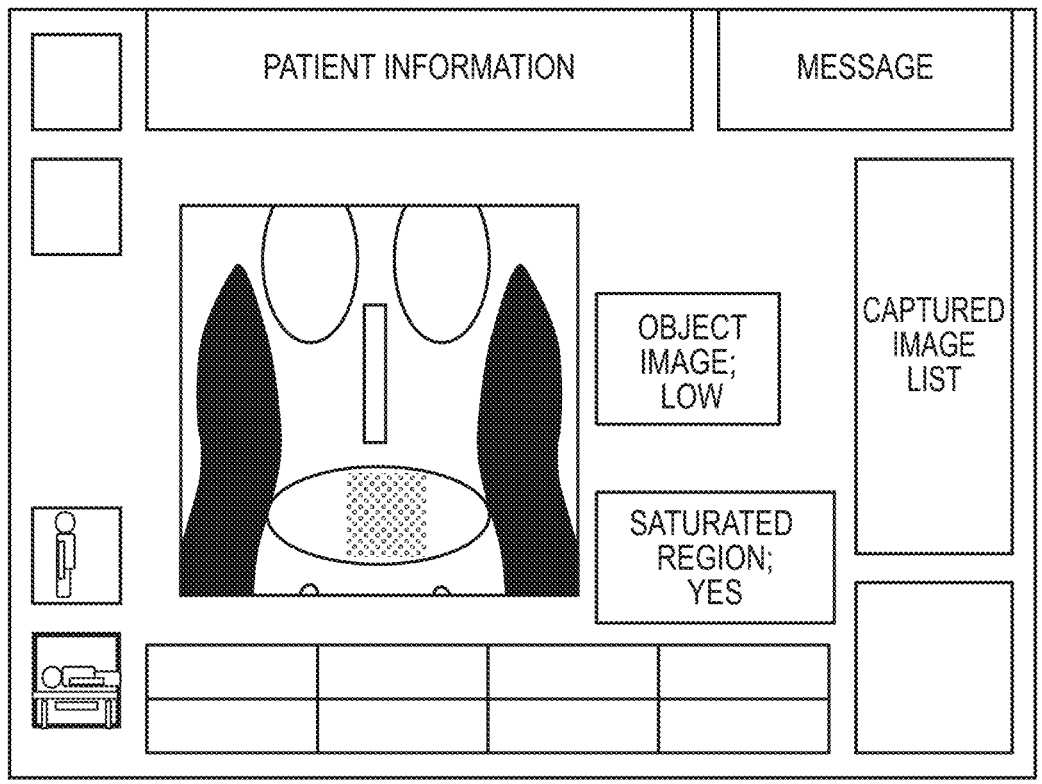
FIG. 11B is a view showing a display example of a sample image.
Figure 11C:
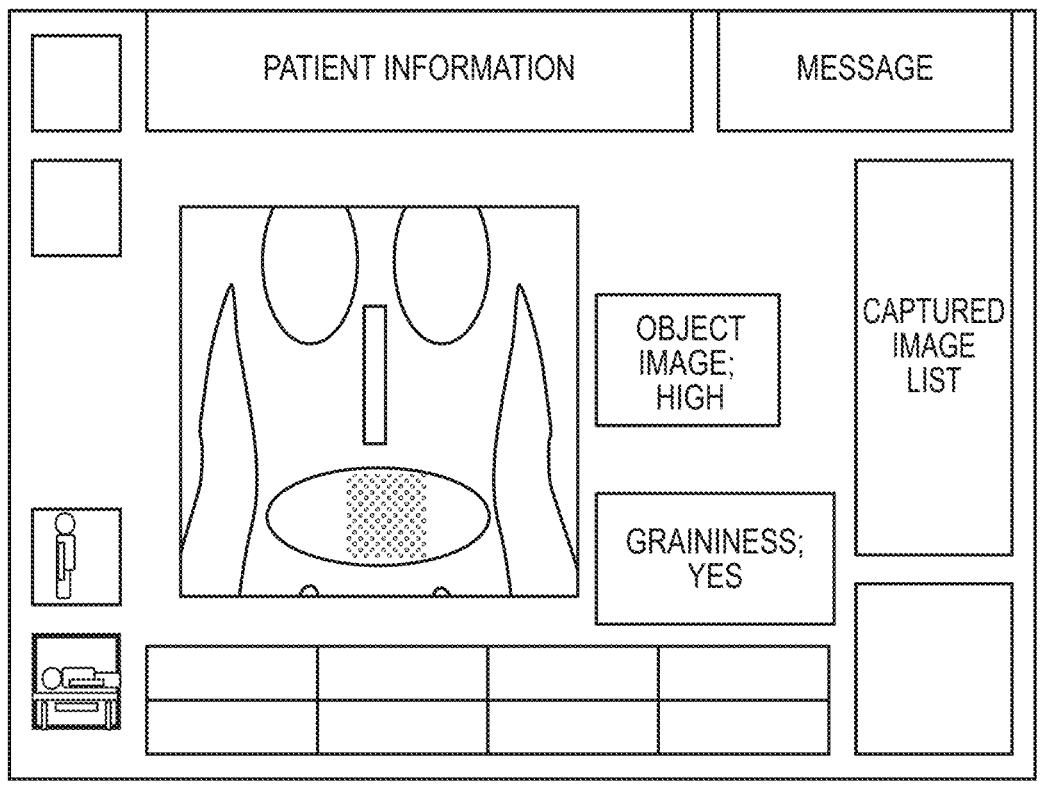
FIG. 11C is a view showing a display example of a sample image.

FIGS. 11A, 11B, and 11C show an example of display of a radiation imaging system and a schematic flowchart for decision on imaging conditions in order to support decision on imaging conditions in this embodiment. The schematic flowchart of FIG. 11A will be described. First of all, the radiographer inputs information related to imaging conditions including a region of interest (step S111). A radiation imaging system 2000 performs simulation to predict an image obtained at the stop of irradiation with radiation as a result of weighting based on the imaging conditions (step S112). The radiation imaging system 2000 then displays this image as a sample image on the display (step S113). A sample image may be generated by performing arithmetic processing for a model image stored in advance based on conditions for imaging to be performed. Alternatively, an image captured previously under similar conditions may be displayed as a sample image. The radiographer looks at the sample image and determines whether the imaging conditions are proper. The radiographer can change imaging conditions such as information related to a region of interest and information related to an imaging dose, the weights of the areas, and a determination formula and input them again. Since a result obtained by re-inputting is displayed on the display again, the radiographer can re-evaluate the imaging conditions.

FIGS. 11B and 11C each show a display example of a sample image. FIG. 11B shows that the set values cause saturated regions. FIG. 11C shows an image with a graininess. When imaging is performed as in these display examples, cautions like "saturated" and "graininess" may be displayed. Images (model images) on which sample images are based may be made selectable from displayed similar captured images by inputting the age, sex, physical size, imaging part, and the like of the object. With respect to a selected model image, an image to be captured when AEC is performed upon weighting based on imaging conditions such as a region of interest is simulated and displayed as a sample image. Looking at the sample image allows the radiographer to know, before imaging, information such as a given region being saturated and blocked up or the graininess of a given region of the object becoming high. This allows the radiographer to have an overall feeling about a captured image without performing preliminary imaging. Accordingly, the radiographer can change the radiation dose of irradiation or the region of interest as needed. This embodiment makes it possible to reduce the redoing of imaging or re-imaging due to imaging errors, input errors, and the like.

Figure 12:
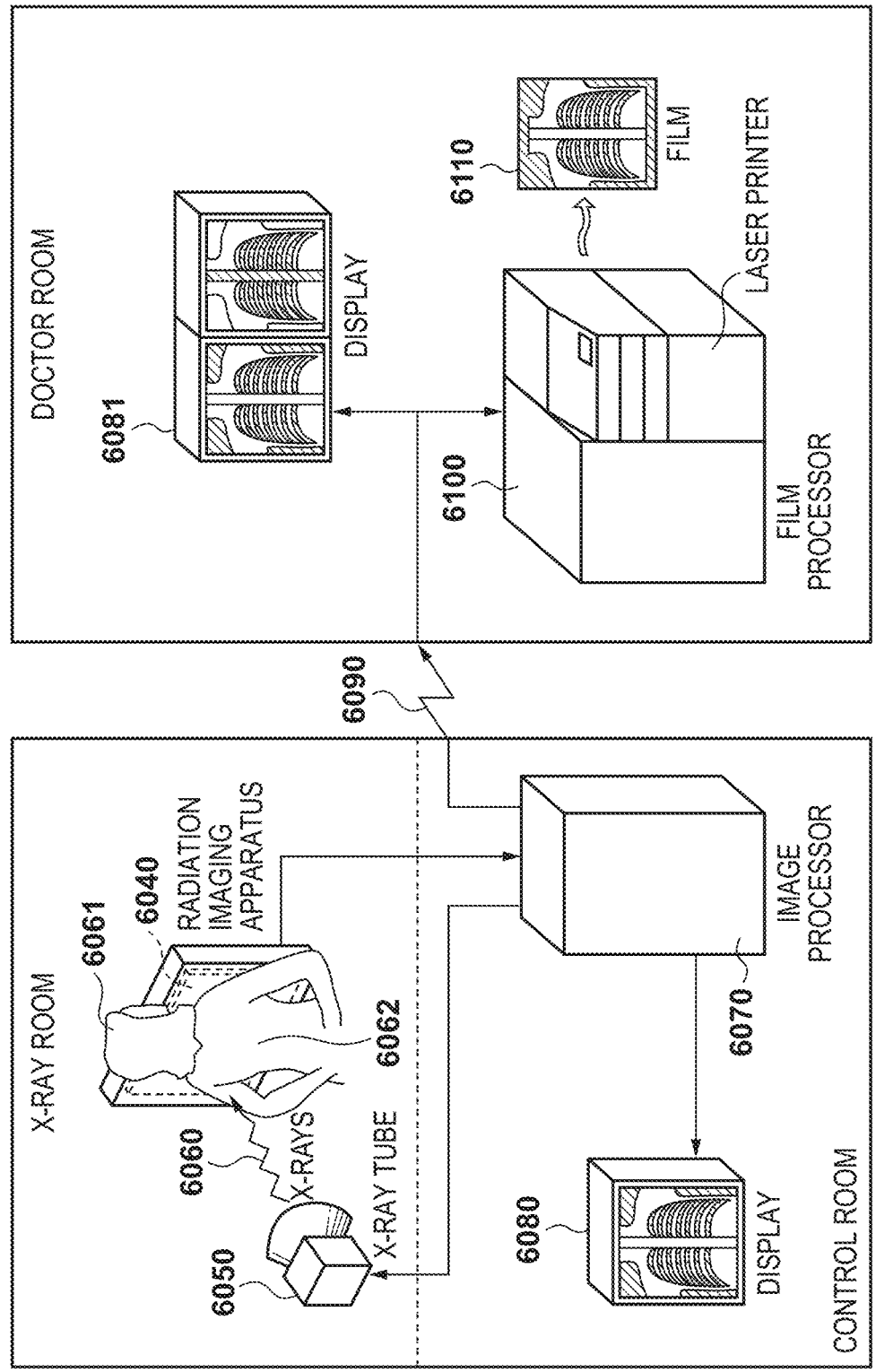
FIG. 12 is a view showing an example of a radiation imaging system.

An example of application of the radiation imaging apparatus according to the present invention to an X-ray diagnosis system will be described next with reference to FIG. 12. An X-ray 6060 generated by an X-ray tube 6050 as a radiation source 1005 passes through a chest 6062 of a patient or object 6061, and enters the scintillator of a radiation imaging apparatus 6040. The incident X-ray contains internal information within the body of the patient or subject 6061. The scintillator emits light in correspondence with the incidence of the X-ray. This light is photoelectrically converted to obtain electrical information. This information is digitally converted, undergoes image processing by an image processor 6070 serving as a signal processor, and can be observed on a display 6080 serving as a display device in the control room. This information can be transferred to a remote place by a transmission processor such as a transmission processor, for example, a telephone line 6090. This makes it possible to display the information on a display 6081 serving as a display device in a doctor room in another place, thus allowing a doctor in a remote place to make a diagnosis. In addition, the information can be recorded on a recording medium such as an optical disk. Furthermore, the information can also be recorded on a film 6110 serving as a recording medium by a film processor 6100 serving as a recording device.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

The present invention can provide a technique advantageous in visualizing an area to be imaged with a proper dose.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:
1. A radiation imaging system, comprising:
a radiation detector having a plurality of pixels configured to detect radiation arrayed in a matrix;
a plurality of detecting pixels arranged in a region in which the plurality of pixels is arrayed in the matrix, and being configured to output a signal corresponding to an amount of irradiation with the radiation;
an input unit; and
a processing unit configured to receive from the input unit an imaging condition including a region of interest, to generate weighting information based on the imaging condition that is associated with the region of interest in an imaging range and assigned to each of a plurality of regions set in the imaging range, and to generate determination information for controlling irradiation with the radiation by applying the weighting information to the corresponding signal, wherein
weighting information assigned to each of the plurality of regions is made to have the same value when the processing unit determines that an irradiation time of radiation based on the imaging condition is shorter than a reference time.

2. The radiation imaging system according to claim 1, wherein the determination information includes a weighted average value of values obtained by the weighting.

3. The radiation imaging system according to claim 1, wherein the determination information includes a value of the corresponding signal.

4. The radiation imaging system according to claim 1, wherein the corresponding signal includes signals from a predetermined number of detecting pixels selected for each of the plurality of regions.

5. The radiation imaging system according to claim 1, wherein the processing unit is configured to generate a condition for stop of irradiation with the radiation based on the imaging condition.

6. The radiation imaging system according to claim 1, further comprising a display configured to display at least one of the imaging condition, a sample image associated with the imaging condition, and the weighting information.

7. The radiation imaging system according to claim 1, wherein the input unit is configured to further receive an input for changing the imaging condition.

8. The radiation imaging system according to claim 1, wherein the imaging condition includes a purpose of imaging.

9. The radiation imaging system according to claim 1, wherein the imaging condition is generated based on an imaging order.

10. The radiation imaging system according to claim 1, further comprising a radiation source configured to generate radiation.

11. A method of generating determination information by a processing unit for controlling irradiation with radiation, the method comprising:
receiving an imaging condition including a region of interest;
generating weighting information, based on the imaging condition, that is associated with a region of interest in an imaging range and which is assigned to each of a plurality of regions set in the imaging range;
reading out a signal corresponding to an amount of irradiation from a plurality of detecting pixels for detecting the amount of irradiation with radiation;
weighting the signal by applying the weighting information to the corresponding signal; and
generating determination information for controlling irradiation with radiation based on the weighted signal, wherein
weighting information assigned to each of the plurality of regions is made to have the same value when the processing unit determines that an irradiation time of radiation based on the imaging condition is shorter than a reference time.

12. A storage medium having instructions stored thereon that are executed by a processing unit of a radiation imaging system to cause the processing unit to:
receive an imaging condition including a region of interest;
generate weighting information, based on the imaging condition, that is associated with a region of interest in an imaging range and which is assigned to each of a plurality of regions set in the imaging range;
read out a signal corresponding to an amount of irradiation from a plurality of detecting pixels for detecting the amount of irradiation with radiation;
weight the signal by applying the weighting information to the corresponding signal; and
generate determination information for controlling irradiation with radiation based on the weighted signal, wherein
weighting information assigned to each of the plurality of regions is made to have the same value when the processing unit determines that an irradiation time of radiation based on the imaging condition is shorter than a reference time.

* * * * *